United States Patent
Lim et al.

(10) Patent No.: US 6,576,161 B2
(45) Date of Patent: Jun. 10, 2003

(54) POLYPHOSPHATE ESTER MORPHOLIDES, MIXTURES THEREOF, AND THERMOPLASTIC RESIN COMPOSITIONS CONTAINING POLYPHOSPHATE ESTER MORPHOLIDES AS FLAME RETARDANTS

(75) Inventors: Jong-Cheol Lim, Kyongki-do (KR); Kyung-Hoon Seo, Seoul (KR); Sam-Joo Yang, Kyongki-do (KR)

(73) Assignee: Cheil Industries, Inc., Kyongsang-Pukdo (KR)

( * ) Notice: Subject to any disclaimer, the term of this patent is extended or adjusted under 35 U.S.C. 154(b) by 0 days.

(21) Appl. No.: 09/997,781

(22) Filed: Nov. 28, 2001

(65) Prior Publication Data

US 2002/0091180 A1 Jul. 11, 2002

Related U.S. Application Data

(63) Continuation-in-part of application No. 09/752,814, filed on Dec. 29, 2000, now Pat. No. 6,437,029.

(30) Foreign Application Priority Data

Oct. 31, 2000 (KR) .......................... 2000-64325
Nov. 28, 2000 (KR) .......................... 2000-71314

(51) Int. Cl.[7] .................. C08K 5/51; C08K 5/357; C07D 413/12; C07D 295/22
(52) U.S. Cl. ................ 252/609; 524/96; 524/97; 528/167; 528/168; 544/84; 544/157
(58) Field of Search .................. 252/609; 524/96, 524/97; 528/168; 544/84, 157

(56) References Cited

U.S. PATENT DOCUMENTS 4,062,909 A * 12/1977 Morgan

FOREIGN PATENT DOCUMENTS

| JP | 59-45351 | 3/1984 |
|---|---|---|
| JP | 59-202240 | 11/1984 |
| JP | 2000-154277 | 6/2000 |

* cited by examiner

Primary Examiner—David J. Buttner
(74) Attorney, Agent, or Firm—Maria Parrish Tungol

(57) ABSTRACT

The present invention relates to polyphosphate ester morpholides, compositions comprising mixtures thereof and thermoplastic resin compositions containing the polyphosphate ester morpholide composition as a flame retardant. The flame retardant compositions comprise mixtures of polyphosphate ester morpholides which are represented by the following general formula I:

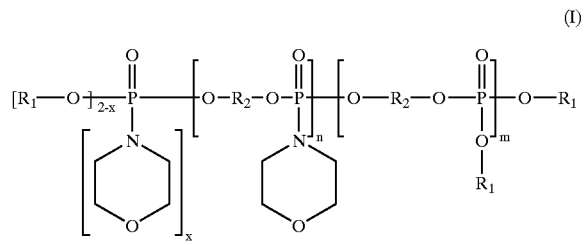

in which X is 1 or 2; $R_1$ is a $C_6$–$C_{20}$ aryl group, an alkyl substituted $C_6$–$C_{20}$ aryl group or a derivative thereof; $R_2$ is a $C_6$–$C_{30}$ arylene group, an alkyl substituted $C_6$–$C_{30}$ arylene group or a derivative thereof; n is the average number of morpholide repeating units, m is the average number of $R_1$ repeating units, and n+m is 1 to 5. In accordance with the present invention, it is possible to provide a flame retardant thermoplastic resin compositions having improved flame retardancy even when small amounts of the flame retardant are used. The thermoplastic compositions according to the present invention also have a desirable balance of properties such as workability, impact strength, heat resistance, appearance and the like.

20 Claims, 6 Drawing Sheets

US 6,576,161 B2

POLYPHOSPHATE ESTER MORPHOLIDES, MIXTURES THEREOF, AND THERMOPLASTIC RESIN COMPOSITIONS CONTAINING POLYPHOSPHATE ESTER MORPHOLIDES AS FLAME RETARDANTS

This application is a continuation-in-part of Ser. No. 09/752,814 filed Dec. 29, 2000 now U.S. Pat. No. 6,437,029.

FIELD OF THE INVENTION

The invention relates to polyphosphate ester morpholides, compositions comprising mixtures thereof, and flame retardant thermoplastic resin compositions containing the same.

BACKGROUND OF THE INVENTION

For a long time it has been a main target in conducting research and development of resins to find a technique to improve flame retardancy of thermoplastic resins. So far, a variety of compounds have been proposed as a flame retardant agent. Flame retardant agents, which are generally used in the thermoplastic resin field, include a flame retardant agent based on a halogenic compound, particularly, a bromic compound, and a phosphorus flame retardant agent based on phosphoric acid ester. Such flame retardant agents are used with a fluorinated polyolefin as a anti-drip agent or an antimony compound as a flame retardation assistant.

However, as concerns about the environmental issue increase, there is a trend to restrain the use of the halogen based flame retardant agent. Therefore, the phosphorus flame retardant agent, which is free of any halogen compound, is preferred to the flame retardant agent. Such a phosphorus flame retardant agent includes monomeric aromatic phosphoric acid ester compounds such as triphenyl phosphate, tricresyl phosphate and the like. The flame retardant agents comprising the monomeric aromatic phosphoric acid ester compounds can provide excellent flame retardancy and desired mechanical properties. However, such a flame retardant agent tends to migrate to the surface of a molded article during a molding process, thereby causing a juicing phenomenon. Furthermore, there is a disadvantage in that heat resistance of the resultant resin composition is remarkably reduced.

Accordingly, in order to overcome the above-mentioned problems, Japanese Patent Laid-Open Publication Nos. Sho59-24736, Sho59-45351, and Sho59-202240 disclose the use of an oligomeric condensed phosphoric acid ester compound as a flame retardant agent for thermoplastic resins. The disclosed flame retardant agents have advantages in that they involve a reduced juicing phenomenon while relatively improving the heat resistance of the resultant resin when they are applied to thermoplastic resins. However, they exhibits a reduced flame retardancy, as compared to that obtained when the same amount of the flame retardant agent based on the monomeric phosphoric acid ester is used. Therefore, it is needed to add the flame retardant agent in an increased amount so as to achieve an equal level of flame retardancy.

Phosphoramide flame retardants are disclosed in Japanese Kokai Publication No. 2000-154277 including phenyl morpholide monophosphate compounds. These compounds are disclosed as flame retardants suitable for use with various synthetic resins. The synthesis of diphenyl morpholide monophosphate and dimorpholide phenyl monophosphate is described. There is no disclosure of derivatives of the monophosphates or reacting the monophosphates with any other compounds.

SUMMARY OF THE INVENTION

The present invention relates to polyphosphate ester morpholides, compositions comprising mixtures thereof and thermoplastic resin compositions containing the polyphosphate ester morpholide composition as a flame retardant. The thermoplastic resin compositions according to the present invention have improved properties such as flame retardancy, mechanical properties, workability, impact strength, heat resistance and the like. The polyphosphate ester morpholides contain a functional group having a nitrogen atom and an oxygen atom have a great electron affinity to the conventional oligomeric phosphoric acid ester compound.

DETAILED DESCRIPTION OF THE PREFERRED EMBODIMENT

Figure 1A:
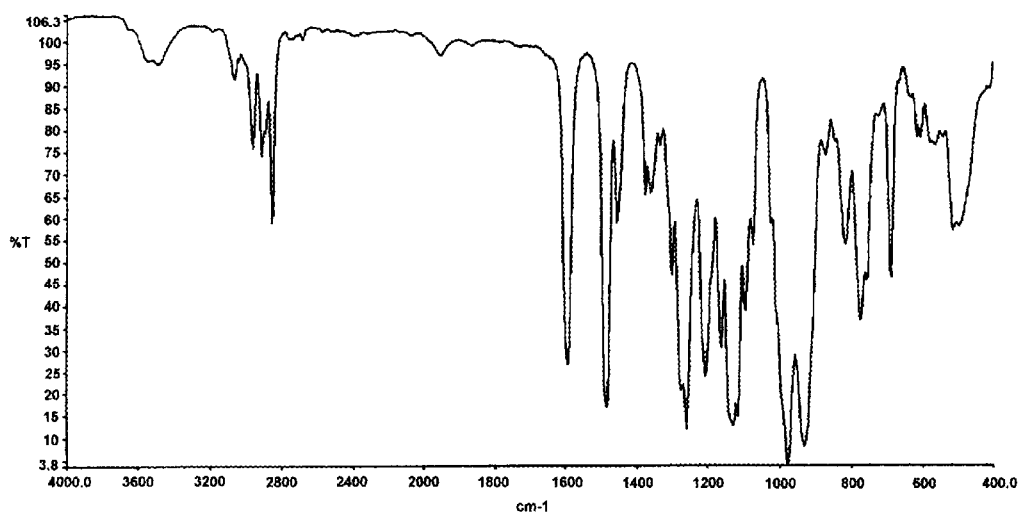
FIGS. 1a, 1b and 1c are graphs illustrating results of IR, NMR and LC analysis respectively, of the polyphosphate ester morpholide composition I used in the examples of the present invention.

According to the present invention, mixtures of polyphosphate ester morpholides are represented by the following general formula I:

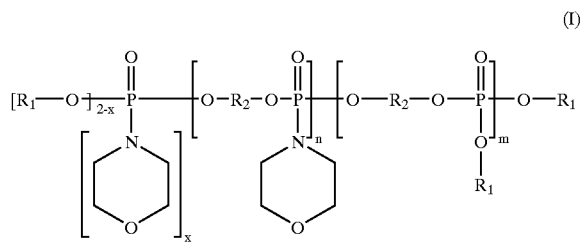

in which X is 1 or 2; $R_1$ is a $C_6$–$C_{20}$ aryl group, an alkyl substituted $C_6$–$C_{20}$ aryl group or a derivative thereof; $R_2$ is a $C_6$–$C_{30}$ arylene group, an alkyl substituted $C_6$–$C_{30}$ arylene group or a derivative thereof; n is the average number of morpholide repeating units, m is the average number of $R_1$ repeating units, and n+m is 1 to 5. The average number of repeating units is also referred to as the number average degree of polymerization.

$R_1$ is preferably a phenyl group or a phenyl group substituted with an alkyl group, for example, methyl, ethyl, propyl, isopropyl, butyl, sec-butyl, tert-butyl, isobutyl, isoamyl, tert-amyl or the like. More preferably, the $R_1$ is a phenyl group, or a phenyl group substituted with methyl, ethyl, isopropyl or tert-butyl group $R_2$ is a residue preferably derived from diphenols such as resorcinol, hydroquinone, bisphenol-A, or alkyl-substituted derivatives thereof. Alkyl-substituted derivatives include resorcinol, hydroquinone, or bisphenol-A having at least one methyl, ethyl, and t-butyl substituents. Preferred alkyl-substituted derivatives have one or two alkyl substituents.

In formula I, n is the average number of morpholide repeating units, m is the average number of $R_1$ repeating units, and and n+m is 1 to 5. The values of n and m can be controlled by known techniques used for known oligomeric polyphosphate esters. When used as a flame retardant in thermoplastic resin compositions, n+m is preferably 1–3, most preferably 1 or 2. It is noted that polyphosphate morpholide compositions wherein n+m is less than 1 can be produced by adding monomeric phosphate morpholide to the morpholide composition or by producing greater amounts of monomeric phosphate morpholide in the reaction mixture during the preparation of the morpholide compositions.

Preferred compositions of polyphosphate ester morpholides are mixtures represented by formula (I) in which about 0 to 20% by weight have m+n=0, about 30 to 100% by weight have m+n =1, and about 0 to 50% by weight have m+n=2 or over.

The polyphosphate ester morpholide compositions of the general formula I are prepared by known methods. The compositions according to the present invention are prepared by reacting an aromatic alcohol containing the $R_1$ group, morpholine, phosphorus oxychloride ($POCl_3$), and a dihydroxy arylene compound containing the $R_2$ group in the presence of an appropriate catalyst.

In a preferred process, the polyphosphate morpholide compositions are prepared first by reacting an aromatic alcohol containing the $R_1$ group and morpholine with phosphorus oxychloride ($POCl_3$) at a temperature of about 50 to 200° C. in the presence of an appropriate catalyst to obtain an aryl morpholino chlorophosphate. The aryl morpholino chlorophosphate is then reacted with a dihydroxy arylene compound containing the $R_2$ group at a temperature of about 70 to 220° C. in the presence of an appropriate catalyst.

Examples of aromatic alcohols containing the $R_1$ group that can be used to prepare the compositions of the present invention include phenol, methyl phenol (cresol), dimethyl phenol, ethyl phenol, diethyl phenol, propyl phenol, isopropyl phenol, butyl phenol, sec-butyl phenol, tert-butyl phenol, di-t-butyl phenol, isobutyl phenol, isoamyl phenol, or tert-amyl phenol. The reaction temperature in this first step is about 50 to 200° C., preferably about 60 to 200° C., most preferably about 60 to 180° C.

Examples of dihydroxy arylene compounds containing the $R_2$ group that can be used include resorcinol, hydroquinone, bisphenol-A, or alkyl-substituted derivatives thereof. Alkyl-substituted derivatives are known in the art and include resorcinol, hydroquinone, or bisphenol-A having at least one methyl, ethyl, or t-butyl substituent. The reaction of the aryl morpholino chlorophosphate and the dihydroxy arylene compound containing the $R_2$ group is conducted at a temperature of about 70 to 220° C., preferably about 70 to 210° C., most preferably about 70 to 200° C.

A polymerization method, which can be used in this procedure, includes a solution polymerization method or a melt polymerization method. The catalyst used to prepare the polyphosphate ester morpholide compositions having the general formula I according to the present invention includes metal chlorides, for example, aluminum chloride ($AlCl_3$), magnesium chloride ($MgCl_2$), zinc chloride ($ZnCl_2$) or the like. Also, it is preferable to add a tertiary amine, for example, triethylamine to remove a by-product resulted from the reaction, that is, HCl.

Alternatively, the dihydroxy arylene compound can be reacted with phosphorus oxychloride ($POCl_3$) in a first reaction step. The resulting product is then reacted with the aromatic alcohol and morpholine. A one step process is also possible but it is more difficult to control the reactions in such a process compared to the two step processes. The synthesized material can be used as it is produced or after being refined.

The synthesized polyphosphate ester morpholide compositions prepared by the above methods may contain morpholides wherein n and m are all 0, in an amount of 0 to 20% by weight depending on the reaction process used. As discussed previously, the amount of morpholides where n and m are 0 can be increased so that n+m is less than 1.

The polyphosphate ester morpholide compositions according to the present invention are comprised of at least one polyphosphate ester morpholide having the following formula (II)

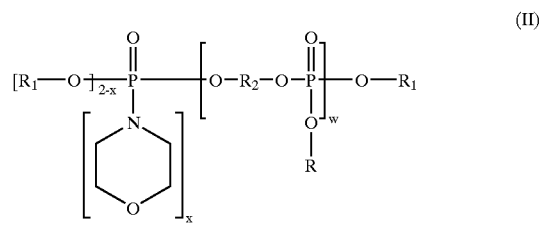

(II)

wherein x is 1 or 2, R is a morpholino group or the same group as $R_1$, w is 1 to 5 and $R_1$ and $R_2$ are groups as described for formula (I). The preferred compositions comprise the previously described mixtures of polyphosphate ester morpholides.

The structures of the polyphosphate ester morpholides in the compositions according to the present invention are determined by conventional methods such as HPLC (high performance liquid chromatography), NMR, and IR analytical data. Compositions produced by the processes described previously are subjected to liquid chromatography. The structures of separated samples are then identified by known NMR and IR analytical techniques.

Polyphosphate ester morpholides in the compositions according to the present invention include those having the following formulas where $R_1$ is a group as defined previously:

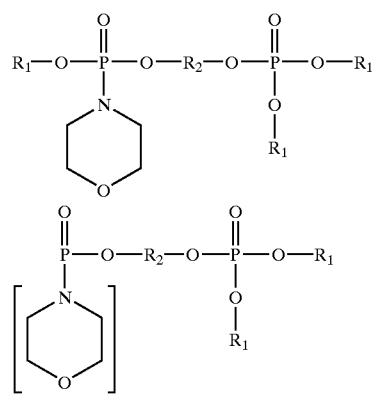

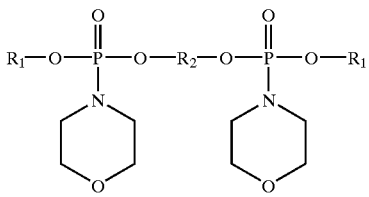

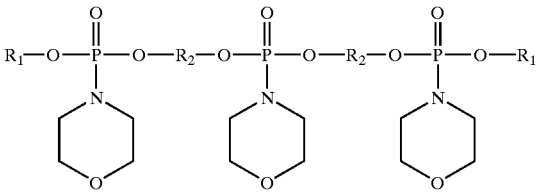

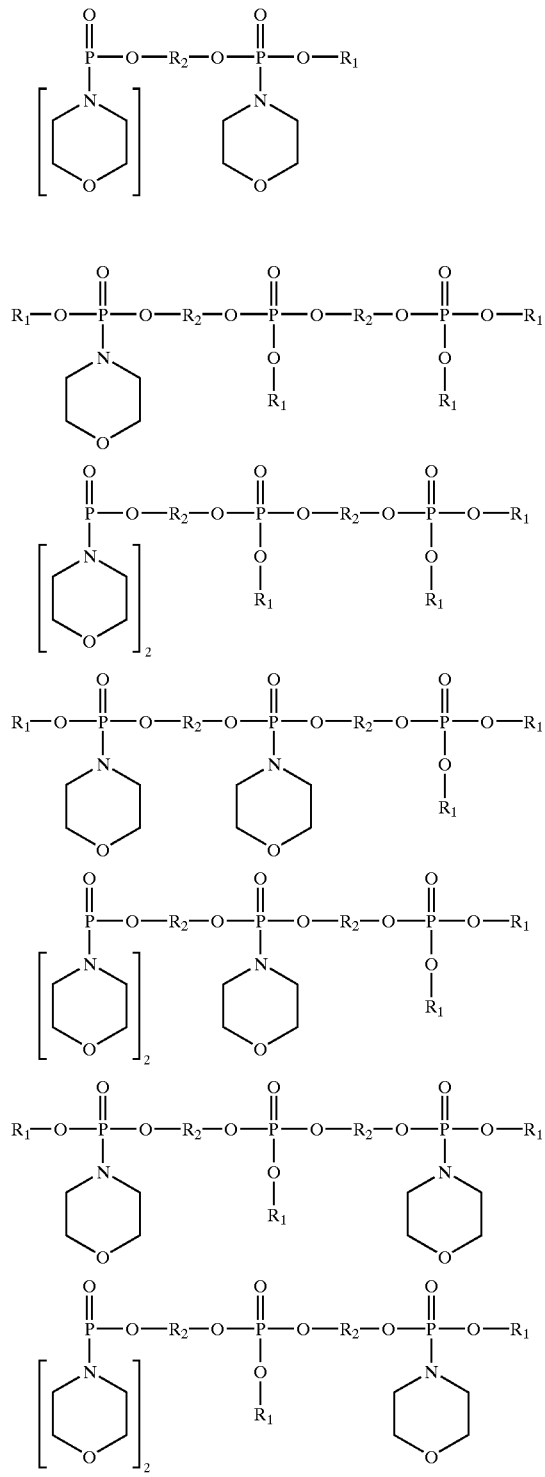

The polyphosphate ester morpholide compositions according to the present invention are used as flame retardants in thermoplastic resin composition which are described hereafter in detail in terms of each component.

(A) Thermoplastic Resin Composition

The thermoplastic resins which can be used to prepare the flame retardant thermoplastic resin compositions according to the present invention are known in the art. Such resin compositions include, but are not limited to, polycarbonate base resins; polyphenylene ether base resins; polyolefin base resins such as polyethylene or polypropylene; polymers based on vinyl carboxylic acid or its derivatives such as polyalkyl acrylate, polyalkyl methacrylate, polyacrylamide, polyacrylonitrile or polyacrylic acid; vinyl aromatic based resin such as polystyrene; diene based resins such as polybutadiene or polyisoprene; polyamide based resins such as nylon 6 or nylon 66; and polyester based resins such as polyethylene terephthalate or polybutylene terephthalate. Also, their copolymers, as well as, their homopolymers can be used. Here, the copolymers may include random, block or grafted compolymers. In addition, a blend of two or more selected from the above-mentioned thermoplastic resins can be used.

The aromatic polycarbonate resin, which can be used according to the present invention, can be prepared by reacting a diphenol expressed by the following general formula IIa with phosgene, halogen formate or carbonic acid diester.

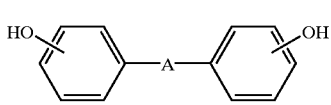

(IIa)

in which A is a single bond, $C_1$–$C_5$ alkylene, $C_1$–$C_5$ alkylidene, $C_5$–$C_6$ cycloalkylidene, —S—, or —$SO_2$—.

Particular examples of the diphenol of the general formula II include hydroquinone, resorcinol, 4,4'-dihydroxydiphenyl, 2,2-bis-(4-hydroxyphenyl)-propane, 2,4-bis-(4-hydroxyphenyl)-2-methylbutan, 1,1-bis-(4-hydroxyphenyl)-cyclohexane, 2,2-bis-(3-chloro-4-hydroxyphenyl)-propane, 2,2-bis-(3,5-dichloro-4-hydroxyphenyl)-propane, and the like.

As the polycarbonate, the one that has a branched chain can be used. Preferably, it can be prepared by adding a tri- or more functional compound, for example, a compound having 3 or more phenol group in an amount of 0.05 to 2 mole % based on the total weight of diphenol used in the polymerization. Also, it is possible to use an aromatic polyester-carbonate resin obtained from the polymerization reaction in the presence of an ester precursor, for example, a bifunctional carboxylic acid.

According to the present invention, the polycarbonate resin has preferably a weight average molecular weight of 10,000 to 200,000, and more preferably a weight average molecular weight of 15,000 to 80,000.

The vinyl aromatic polymer which can be used according to the present invention includes vinyl aromatic copolymers resulted from the copolymerization of 50 to 95% by weight of styrene, α-methylstyrene, halogen, alkyl substituted styrene or a mixture thereof, and 5 to 50% by weight of acrylonitrile, methacrylonitrile, $C_1$–$C_8$ methacrylic acid alkyl ester, $C_1$–$C_8$ acrylic acid alkyl ester, maleic anhydride, $C_1$–$C_4$ alkyl, or phenyl nuclei substituted maleimide or a mixture thereof. Also, a blend of two or more copolymers can be used.

The $C_1$–$C_8$ methacrylic acid alkyl ester or $C_1$–$C_8$ acrylic acid alkyl ester belongs to a class of methacrylic acid esters or acrylic acid esters, respectively. Both of them are esters derived from monohydril alcohol having 1 to 8 carbon atoms. Examples of the $C_1$–$C_8$ methacrylic acid alkyl ester or $C_1$–$C_8$ acrylic acid alkyl ester may include methacrylic acid methyl ester, methacrylic acid ethyl ester, acrylic acid methyl ester, acrylic acid ethyl ester, and methacrylic acid propyl ester. The methacrylic acid methyl ester may be particularly preferred.

The preferable vinyl aromatic copolymer includes copolymers of styrene, acrylonitrile and methacrylic acid methyl ester monomer which may be selectively included, copolymers of α-methylstyrene, acrylonitrile and methacrylic acid methyl ester monomer which may be selectively included, copolymers of styrene, α-methylstyrene, acrylonitrile and methacrylic acid methyl ester monomer which may be selectively included, and the like. This copolymer is usually prepared by the conventional emulsion polymerization method, suspension polymerization method or bulk polymerization method. According to the present invention, it is preferred to use the copolymer having a weight average molecular weight of 15,000 to 200,000.

As another preferred vinyl aromatic copolymer, a copolymer of styrene and maleic anhydride may be used. Preferably, the content of maleic anhydride is in a range of 5 to 50% by weight, although the compositional ratio of the two components can be varied in a broad range. This copolymer also can be prepared by the conventional continuous bulk polymerization method or solution polymerization method. According to the present invention, it is preferred to use such vinyl aromatic copolymer having a weight average molecular weight of 20,000 to 200,000 and an intrinsic viscosity of 0.3 to 0.9.

Further, as the vinyl aromatic copolymer which can be used according to the present invention, rubber modified graft copolymers may be used. The vinyl aromatic rubber modified graft copolymer can be prepared by graft polymerizing 5 to 95 part by weight of a monomer mixture composed of 50 to 95% by weight of styrene, α-methylstyrene, halogen, alkyl substituted styrene or a mixture thereof and 5 to 50% by weight of acrylonitrile, methacrylonitrile, a $C_1$–$C_8$ methacrylic acid alkyl ester, a $C_1$–$C_8$ acrylic acid alkyl ester, maleic anhydride, a $C_1$–$C_4$ alkyl, phenyl nuclei-substituted maleimide or a mixture thereof onto 5 to 95 part by weight of a rubber polymer, for example, butadiene rubber, acryl rubber, ethylene/propylene rubber, styrene/butadiene rubber, acrylonitrile/butadiene ruber, isoprene rubber, ethylene-propylene-diene rubber (EPDM), a polyorganosiloxane/polyalkyl (meth)acrylate rubber composite or a mixture thereof.

The $C_1$–$C_8$ methacrylic acid alkyl ester or $C_1$–$C_8$ acrylic acid alkyl ester belongs to a class of methacrylic acid esters or acrylic acid esters, respectively. Both of them are esters derived from monohydril alcohol having 1 to 8 carbon atoms. Examples of the $C_1$–$C_8$ methacrylic acid alkyl ester or $C_1$–$C_8$ acrylic acid alkyl ester may include methacrylic acid methyl ester, methacrylic acid ethyl ester, acrylic acid methyl ester, acrylic acid ethyl ester, and methacrylic acid propyl ester. Methacrylic acid methyl ester is particularly preferred.

The preferred vinyl aromatic rubber modified graft copolymer according to the present invention includes copolymers obtained from graft copolymerization of a mixture of styrene, acrylonitrile and (meth)acrylic acid alkyl ester monomer which may be selectively included, to butadiene rubber, acryl rubber or styrene/butadiene rubber. Among them, particular preference is given to ABS graft copolymers.

The method for producing the above graft copolymer includes the conventional emulsion polymerization method, suspension polymerization method, solution polymerization method or bulk polymerization method. In accordance with the preferred embodiment of the present invention, the rubber modified graft copolymer is prepared by introducing the above-mentioned aromatic vinylic monomer in the presence of a rubbery polymer and conducting emulsion polymerization or bulk polymerization using a polymerization initiator. Preferably, the rubber has a size of 0.05 to 4 μm in order to improve impact strength and surface properties of the molded articles.

The polyphenylene ether base resins which can be use in the present invention can be used alone or in a combination with styrene base polymer.

Particular examples of polyphenylene ether base resin include poly(2,6-dimethyl-1,4-phenylene)ether, poly(2,6-diethyl-1,4-phenylene)ether, poly(2,6-dipropyl-1,4-phenylene)ether, poly(2-methy-6-ethyl-1,4-phenylene) ether, poly(2-methyl-6-propyl-1,4-phenylene)ether, poly(2-ehtyl-6-propyl-1,4-phenylene)ether, poly(2,6-diphenyl-1,4-phenylene)ether, copolymers of (2,6-dimethyl-1,4-phenylene)ether and (2,3,6-trimethyl-1,4-phenylene)ether, and copolymers of (2,6-dimethyl-1,4-phenylene)ether and (2,3,6-triethyl-1,4-phenylene)ether. Among these polyphenylene ether, copolymers of (2,6-dimethyl-1,4-phenylene) ether and (2,3,6-trimethyl-1,4-phenylene)ether or poly(2,6-dimethyl-1,4-phenylene)ether are preferred. In particular, poly(2,6-dimethyl-1,4-phenylene)ether is more preferred.

The degree of polymerization of the polyphenylene ether resin used to prepare the resin composition according to the present invention is not particularly limited. However, taking thermal stability or workability of the resin composition into the consideration, the polyphenylene ether resin has preferably an intrinsic viscosity of 0.2 to 0.8 as measured in chloroform solvent at 25° C. Also, the polyphenylene ether resin can be used alone or as a mixuture of two or more in an appropriate ratio.

Further, the polyphenylene ether resin can be used in a mixture with a styrenic polymer. Such styrenic polymer includes polystyrene, high impact polystyrene (HIPS), polychlorostyrene, poly α-methylstyrene, poly tert-butylstyrene or a copolymer thereof. The above-mentioned polymers can be used alone or as a mixture of two or more in an appropriate ratio. The weight ratio of polyphenylene ether resin and styrenic polymer is preferably in the range of 5:95 to 95:5. It is most preferred to use polystyrene or high impact polystyrene. Preferably, the weight average molecular weight of the styrenic resin is 20,000 to 500,000, taking thermal stability and workability of the resin composition into consideration, although it is not particularly limited.

The polyamide base resin which can be used in the present invention includes polycaprolactam (nylon 6), poly(11-aminoundecanoic acid) (nylon 11), polylauryllactam (nylon 12), polyhexamethylene adiphamide (nylon 6,6), polyhexamethylene azelamide (nylon 6,9), polyhexamethylene cevacamide (nylon 6, 10), polyhexamethylene dodecanodiamide (nylon 6,12), or copolymers thereof, for example, nylon 6/6,10, nylon 6/6,6, nylon 6/12. These resins also can be used alone or as a mixture of two or more in an appropriate ratio. However, it is desirable to select a polyamide resin having a melting point of not less than 200° C. and a relative viscosity of not less than 2.0 as measured at 25° C. when adding 1% by weight of polyamide resin to m-cresol, taking mechanical properties and heat resistance of the resin composition into consideration.

The polyester base resin which can be used in the present invention includes polyalkene dicarboxylates. In general, they can be prepared by reacting one or more of diol such as ethylene glycol, 1,2-propylene glycol, 1,4-butandiol, 1,3-butylene glycol, 1,4-cyclohexanedimethanol, bisphenol-A with one or more of aromatic dicarbonic acid such as isophthalic acid, terephthalic acid, alkyl esters thereof.

Also, in accordance with the present invention, the polyester base resin includes polyethylene terephthalate resins or copolymers thereof and polybutylene terephthalate resins. As the polyethylene terephthalate base copolymers, copolymerized resins comprising mainly polyethylene terephthalate and 20 to 30% of isophthalic acid, 1,2-propylene glycol and 1,3-butylene glycol, as well as polyester resulted from the terephthalic acid and ethylene glycol can be included.

Since hydrolysis often occurs during the extruding process or molding process of the resin, it is preferred to remove water from the polyester base resin before using it. Preferably, the weight average molecular weight of the polyester base resin is 20,000 to 70,000, taking mechanical properties and heat resistance of the resin composition into consideration, although it is not particularly limited.

As the thermoplastic resin used to produce the resin composition according to the present invention, polycarbonates, polyphenylene ethers, polyesters, styrenic polymers, styrene-acrylonitrile copolymers, acrylonitrile-butadiene-styrene copolymers are preferred. They can be used alone or as a mixture. A mixture such as polyphenylene ether/styrenic polymer (including HIPS), polyphenylene ether/acrylonitrile-butadien-styrene copolymer (including styrene-acrylonitrile copolymer), polycarbonate/acrylonitrile-butadiene-styrene copolymer (including styrene-acrylonitrile copolymer) or polycarbonate/polyester is preferred.

Preferred resin components of the thermoplastic resin compositions according to the present invention having desirable mechanical properties include a mixture of about 5~95 parts by weight of polyphenylene ether and about 5~95 parts by weight of styrenic polymer, a mixture of about 10~90 parts by weight of polyphenylene ether, about 5~90 parts by weight of acrylonitrile-butadiene-styrene copolymer, and optionally 0~50 parts by weight of styrene-acrylonitrile copolymer, a mixture of about 30~95 parts by weight of polycarbonate, about 1~50 parts by weight of acrylonitrile-butadiene-styrene copolymer and optionally 0~50 parts by weight of styrene-acrylonitrile copolymer, and a mixture of about 5~95 parts by weight of polycarbonate and about 5~95 parts by weight of polyester.

(B) Polyphosphate Ester Morpholide Composition

Flame retardant thermoplastic resin composition according to the present invention contain compositions of polyphosphate ester morpholide mixtures represented by the general formula I as the flame retardant. Polyphosphate ester morpholide compositions comprised of mixtures having the formula (III) described hereafter may also be used as flame retardants.

Preferably, the polyphosphate ester morpholide composition is added in an amount of 1 to 35 parts by weight based on 100 parts by weight of the thermoplastic resin. When less than 1 part by weight is added, little or no flame retardancy is observed. When more than 35 parts by weight is used, the flame retardancy is not significantly improved The flame retardant thermoplastic resin compositions according to the present invention may further comprise commercially available flame retardant agent and flame retardation assistant other than the above-described polyphosphate ester morpholide composition, for example, a monomeric phosphoric acid ester morpholide compound, other organic phosphoric acid ester compound, a halogen-containing organic compound, a cyanurate compound, a metal salt, a fluorinated polyolefin and the like in order to improve flame retardancy.

The organic phosphoric acid ester compounds which can be used includes monomeric phosphoric acid ester compounds such as triphenyl phosphate or tricresylphosphate and oligomeric condensed phosphoric acid ester derived from divalent alcohol such as resorcinol, hydroquinone, bisphenol-A.

The metal salt which can be used as the flame retardation assistant includes the conventionally well-known sulphonic acid metal salts. The fluorinated polyolefinic resin which can be used as the anti-drip agent includes polytetrafluoroethylenes, polyvinylidene fluorides, tetrafluoroethylene/vinylidenefluoride copolymers, tetrafluoroethylene/hexafluoropropylene copolymers and ethylene/tetrafluoroethylene copolymers. These resins can be used alone or in a combination of two or more.

In addition, the flame retardant thermoplastic resin composition according to the present invention may includes ordinary additives such as lubricant, releasing agent, nucleating agent, antistatic agent, stabilizer, a reinforcing material, inorganic additives, pigment or dye. The inorganic additives can be used in an amount of 0.1 to 60 parts by weight and preferably 1 to 40 parts by weight based on 100 parts by weight of the base thermoplastic resin.

The flame retardant thermoplastic resin composition of the present invention can be prepared by the conventional resin composition producing methods. For example, components of the present invention and other additives are mixed together, and melt-extruded in an extruder to produce the composition in a pellet form.

The flame retardant thermoplastic resin composition of the present invention can be used in molding of various articles. Particularly, it is suitable for housings and internal parts of electric and electronic appliances that need superiority in flame retardancy, heat resistance, mechanical properties, and moldability.

Thermoplastic resin compositions containing polyphosphate ester morpholide compositions according to the present invention are disclosed in copending Ser. No. 09/752,814 herein incorporated by reference. These compositions include flame retardant thermoplastic resin compositions comprising:

(A) about 45 to 95 parts by weight of a polycarbonate resin;

(B) about 1 to 50 parts by weight of a rubber modified styrene-grafted copolymer prepared by graft-polymerizing
  ($b_1$) about 5 to 95 parts by weight of a monomer mixture comprising about 50 to 95% by weight of styrene, α-methylstyrene, halogen- or alkyl-substituted styrene or a mixture thereof and about 5 to 50% by weight of acrylonitrile, methacrylonitrile, maleic acid anhydride, $C_{1-4}$ alkyl- or phenyl N-substituted maleimide or a mixture thereof
  onto ($b_2$) about 5 to 95 parts by weight of a rubber polymer selected from the group consisting of butadiene rubber, acryl rubber, ethylene-propylene rubber, styrene-butadiene rubber, acrylonitrile-butadiene rubber, isoprene rubber, copolymer of ethylene-propylene-diene (EPDM), polyorganosiloxane-polyalkyl(meth)acrylate rubber or a mixture thereof;

(C) about 0.5 to 50 parts by weight of a styrene-containing copolymer polymerized with
  ($c_1$) about 50 to 95% by weight of styrene, α-methylstyrene, halogen- or alkyl-substituted styrene or a mixture thereof and
  ($c_2$) about 5 to 50% by weight of acrylonitrile, methacrylonitrile, maleic acid anhydride, $C_{1-4}$ alkyl- or phenyl N-substituted maleimide or a mixture thereof;

(D) about 0.5 to 50 parts by weight of a (meth)acrylic acid ester copolymer polymerized with
  ($d_1$) about 44 to 90% by weight of a methacrylic acid alkyl ester, a $C_{1-8}$ acrylic acid alkyl ester, or a mixture thereof,
  ($d_2$) about 5 to 55% by weight of styrene, α-methylstyrene, halogen- or alkyl-substituted styrene or a mixture thereof and
  ($d_3$) about 1 to 20% by weight of acrylonitrile, methacrylonitrile, or a mixture thereof;

(E) about 1 to 30 parts by weight of a polyphosphate ester morpholide composition as a flame retardant; and (F) about 0.05 to 5.0 parts by weight of a fluorinated polyolefin resin with average particle size of about 0.05 to 1000 μm and density of about 1.2 to 2.3 g/cm³ as per 100 parts by weight of (A)+(B)+(C)+(D), wherein the polyphosphate ester morpholide composition is represented by the following formula (III):

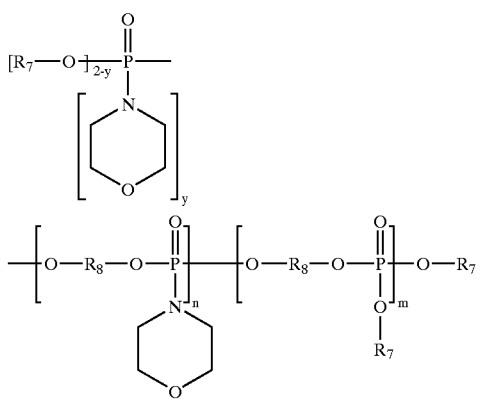

where $R_7$, is a $C_{6-20}$ aryl group or an alkyl-substituted $C_{6-20}$ aryl group, $R_8$ is a $C_{6-30}$ aryl group or an alkyl-substituted $C_{6-30}$ aryl group, y is 1 or 2, and n is the average number of morpholide repeating units, m is the average number of $R_7$ repeating units, and m+n is 0 to 3. Possible $R_7$ groups include the $R_1$ groups described previously. Preferred $R_7$ include a phenyl group or an alkyl-substituted phenyl group in which alkyl is methyl, ethyl, isopropyl or t-butyl. Examples of $R_8$ include the groups described previously for $R_2$. Preferred $R_8$ groups include resorcinol, hydroquinone or bisphenol-A.

Another embodiment of flame retardant thermoplastic resin composition according to the present invention are compositions comprising:

(A) about 70 to 80 parts by weight of a polycarbonate resin;

(B) about 10 parts by weight of a rubber modified styrene-grafted copolymer prepared by graft-polymerizing
  ($b_1$) about 5 to 95 parts by weight of a monomer mixture comprising about 36 parts by weight of styrene and about 14 parts by weight of acrylonitrile,
  ($b_2$) about 45 parts by weight of a butadiene rubber;

(C) about 5 to 10 parts by weight of a styrene-containing copolymer polymerized with
  ($c_1$) about 75 parts by weight of styrene, and
  ($c_2$) about 29 parts by weight of acrylonitrile;

(D) about 5 to 13 parts by weight of a (meth)acrylic acid ester copolymer polymerized with
  ($d_1$) about 70 parts by weight methacrylic acid ester,
  ($d_2$) about 20 parts by weight of styrene, and
  ($d_3$) about 10 parts by weight of acrylonitrile;

(E) about 2 to 12 parts by weight of a polyphosphate ester morpholide composition as a flame retardant; and (F) about 0.4 parts by weight of a fluorinated polyolefin resin with average particle size of about 0.05 to 1000 μm and density of about 1.2 to 2.3 g/cm³ as per 100 parts by weight of (A)+(B)+(C)+(D), wherein the polyphosphate ester morpholide composition (E) is represented by the following formula (III):

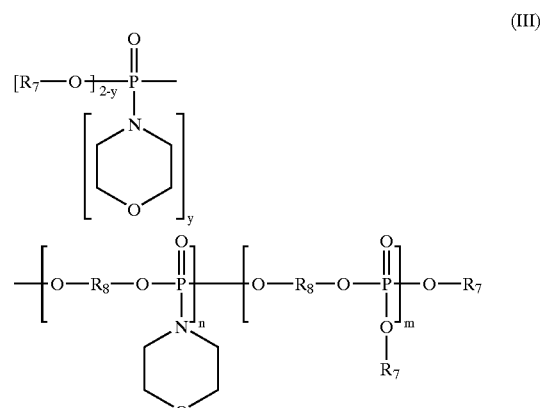

where $R_7$ is a phenyl group, $R_8$ is a resorcinol or an alkyl substituted derivative thereof wherein the morpholide composition is comprised of 1.5% by weight having m+n=0 and y=1, 68.4% by weight having m+n=1, and y=1, and 30.1% by weight having m+n≧2 and y=1.

Now, the present invention will be described in detail, with reference to examples. However, they are given for the purpose of explanation but not for limitation of the present invention.

PREPARATION EXAMPLES

Figure 1B:
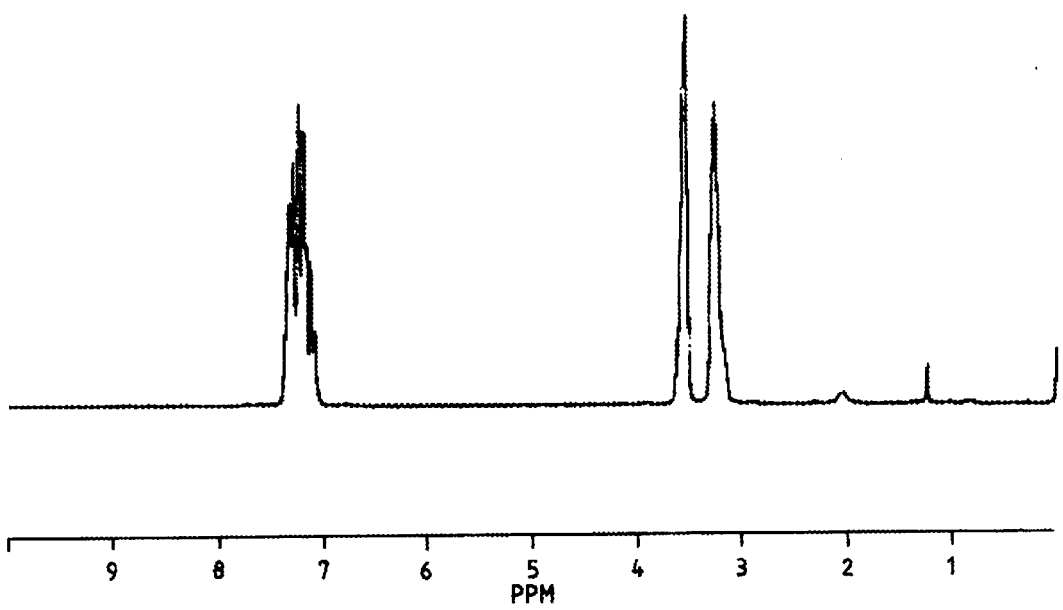
Figure 1C:
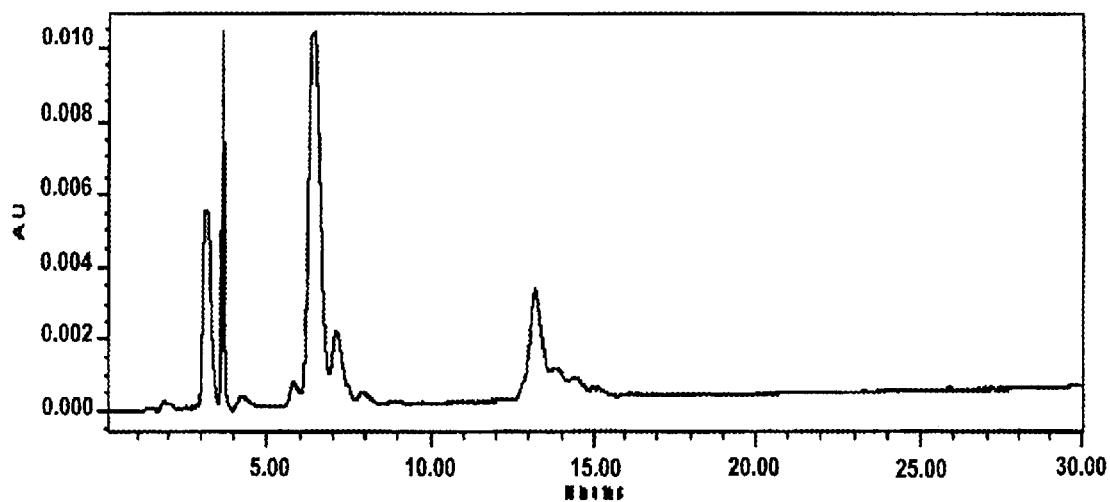

A. Preparation of Polyphosphate Ester Morpholide Compositions and Phosphoric Acid Ester Compound (A-1) Polyphosphate Ester Morpholide Composition I 307 g (2 moles) of phosphorus oxychloride, 188 g (2 moles) of phenol, 174 g (2 moles) of morpholine, 4 g of aluminum chloride, and 900 g of triethylamine were charged into a four-neck flask equipped with a thermometer, condenser, stirrer, dropping instrument. After heating to a temperature of 140° C., the mixture was reacted for 2 hours under an atmosphere of $N_2$. 110 g (1 mole) of resorcinol was further added, heated to a temperature 160° C. and reacted for 4 hours under an atmosphere of $N_2$. The reaction mixture was then washed with deionized water. Catalyst and other impurities were removed to obtain 510 g of polyphosphate ester morpholide composition I having the characteristics as listed below. The results of IR, NMR and LC (Liquid Chromatography) analysis are shown in FIGS. 1a, 1b and 1c, respectively. Unless otherwise indicated, the percentages are by weight.

Characteristics of Polphosphate Ester Morpholide Composition I

Appearance: Viscous light red liquid phase
Phosphorus content: 11.2%
Acid value (KOHmg/g): 0.32
LC data: n+m is 0; 1.5,
n+m is 1; 68.4%,
n+m is 2 or more; 30.1.
(n and m are as defined in the general formula I)
IR data: 2857, 2895, 2917, 2965 cm$^{-1}$ (—$CH_2$—)
NMR data: 3.2 to 3.6 ppm (—$CH_2$—)

Figure 2A:
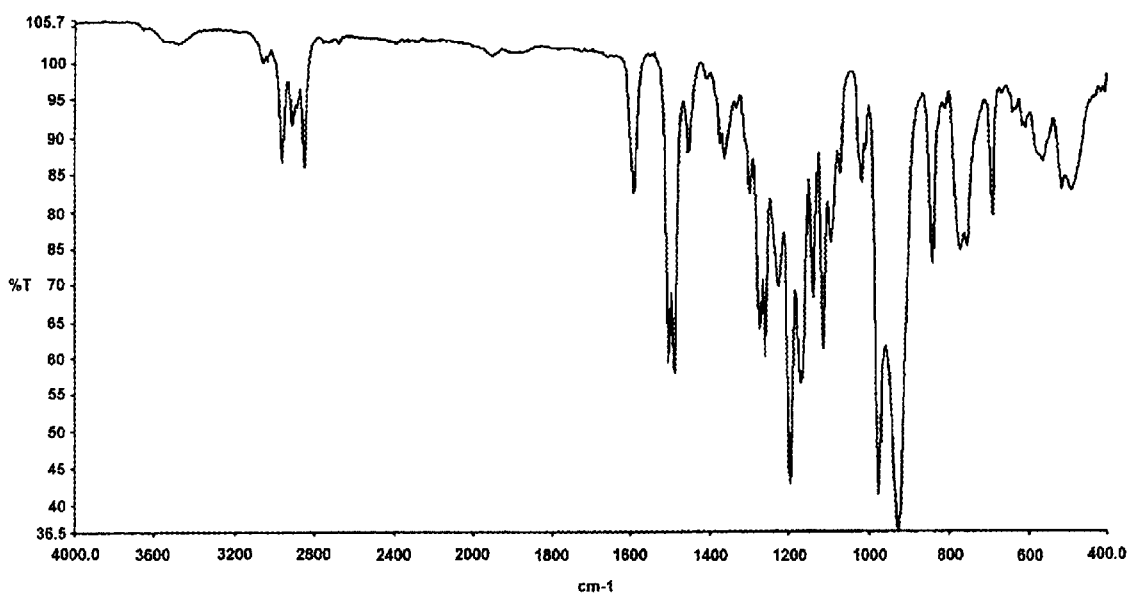
FIGS. 2a, 2b and 2c are graphs showing results of IR, NMR and LC analysis respectively, of polyphosphate ester morpholide composition II used in the examples of the present invention.
Figure 2B:
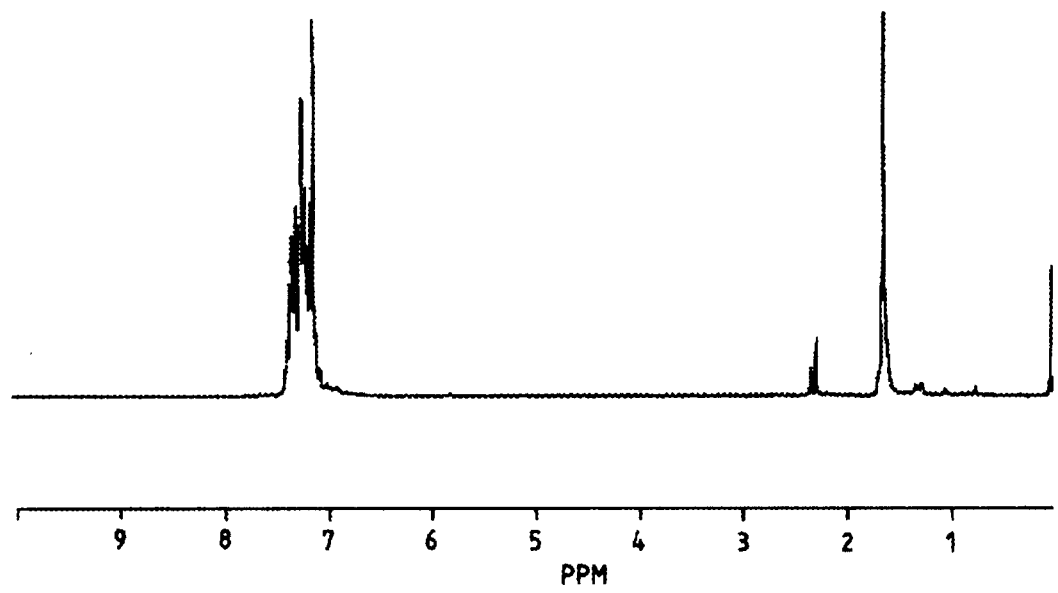
Figure 2C:
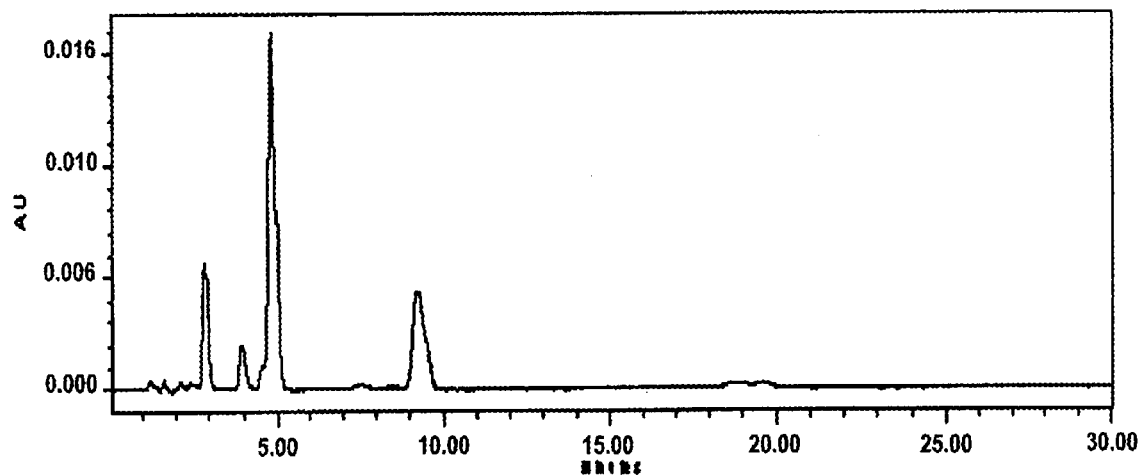

(A-2) Polyphosphate Ester Morpholide Composition II 307 g (2 moles) of phosphorus oxychloride, 87 g (1 mole) of morpholine, 4 g of aluminum chloride, and 150 g of triethylamine were charged into a four-neck flask equipped with a thermometer, condenser, stirrer, dropping instrument. After heating to a temperature of 130° C., the mixture was reacted for 2 hours under an atmosphere of $N_2$. Then 188 g (2 moles) of phenol and 108 g (1 mole) of cresol were further added, heated to a temperature 150° C. and reacted for 2 hours under an atmosphere of $N_2$. 228 g (1 mole) of bisphenol-A was added, heated to a temperature 180° C. and reacted for 4 hours under an atmosphere of $N_2$. The reaction was then washed with deionized water. Catalyst and other impurities were removed to obtain 611 g of polyphosphate ester morpholide composition II having characteristics as listed below. The results of IR, NMR and LC (Liquid Chromatography) analysis are shown in FIGS. 2a, 2b and 2c, respectively.

Characteristics of Phosphoric Acid Ester Morpholide Compound II

Appearance: Highly viscous light brown liquid phase
Phosphorus content: 9.0%
Acid value (KOHmg/g): 0.3
LC data: n+m is 0; 3.1%,
n+m is 1; 84.7%,
n+m is 2 or more; 12.2%.
(n and m are as defined in the general formula I)
IR data: 2856, 2916, 2967 cm$^{-1}$ (—$CH_2$—)
NMR: 1.6 ppm (—$CH_3$), 3.2 to 3.6 ppm (—$CH_2$—)

(A-3) Phosphoric Acid Ester Compound I

Figure 3A:
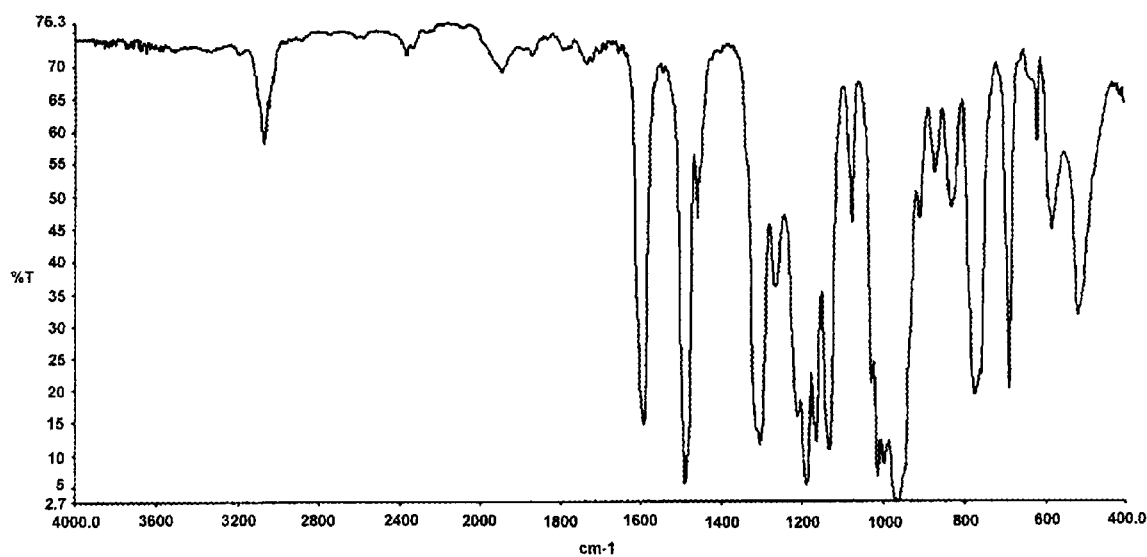
FIGS. 3a and 3b are graphs showing results of IR and NMR analysis respectively, of polyphosphate ester composition I used in the comparative examples of the present invention.
Figure 3B:
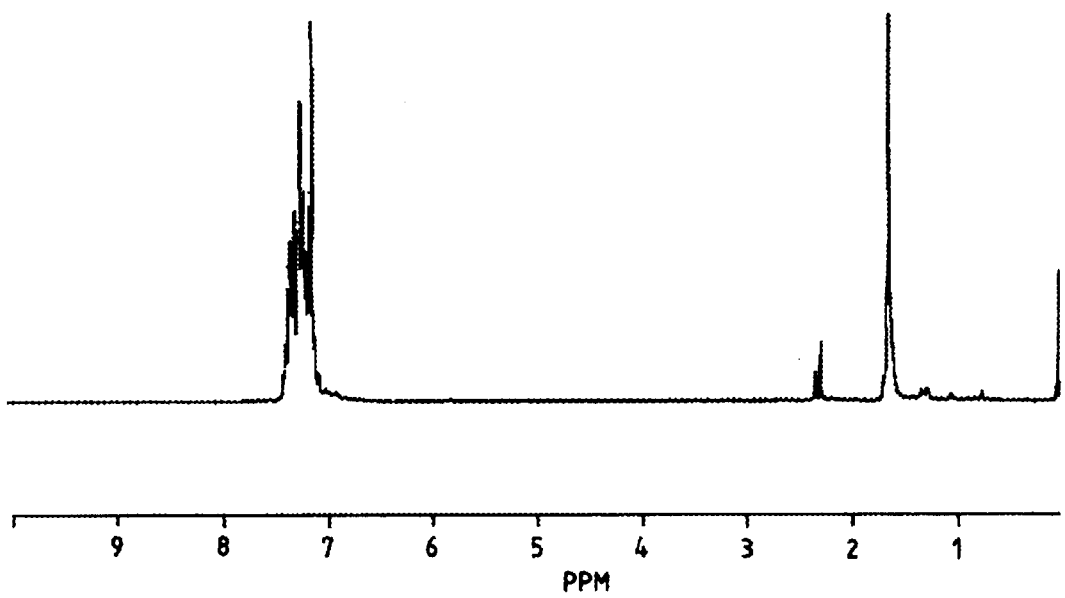

As a comparative compound herein, an oligomeric phosphoric acid ester compound I derived from a resorcinol was used. It was CR-733S supplied from Daihachi Chemical Company (Japan), which comprised 2.5% by weight of a monomeric phosphoric acid ester compound, 67.2% by weight of an oligomeric phosphoric acid ester compound having a number average polymerization degree of 1, and 30.3% by weight of an oligomeric phosphoric acid ester compound having a number average polymerization degree of not less than 2. This phosphoric acid ester compound I had characteristics as listed below. The results of IR and NMR analysis are shown in FIGS. 3a and 3b, respectively.

Characteristics of Phosphoric Acid Ester Compound I

Appearance: Transparent and viscous liquid phase
Phosphorus content: 10.9%
Acid value (KOHmg/g): 0.1
LC data: m is 0; 2.5%,
m is 1; 67.2%,
m is 2 or more; 30.3%.
(m represents degree of polymerization)

(A-4) Phosphoric Acid Ester Compound II

Figure 4A:
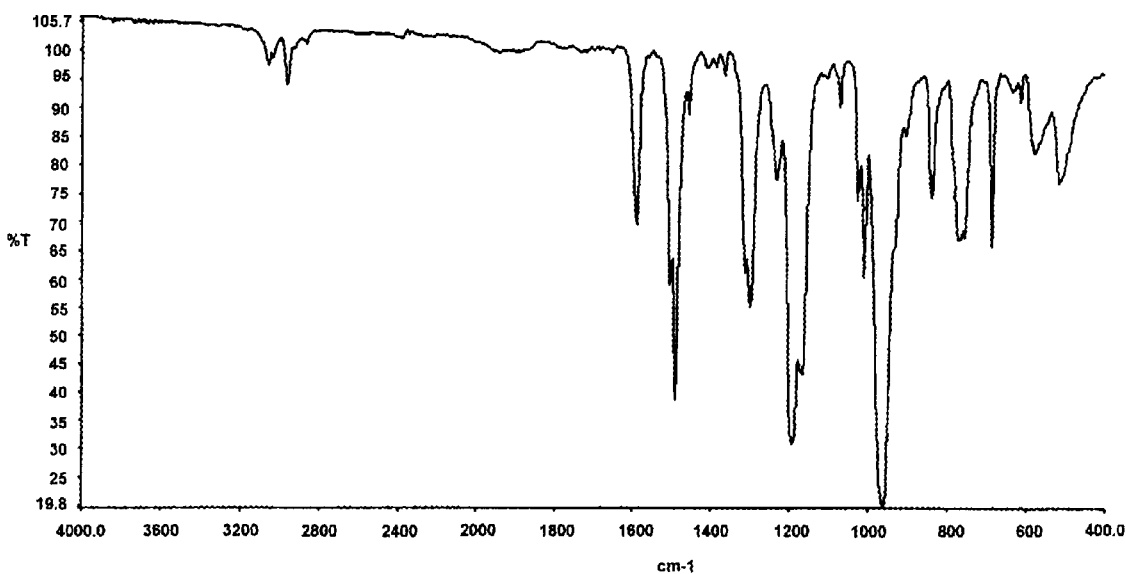
FIGS. 4a and 4b are graphs showing results of IR and NMR analysis respectively, of polyphosphate ester composition II used in the comparative examples of the present invention.
Figure 4B:
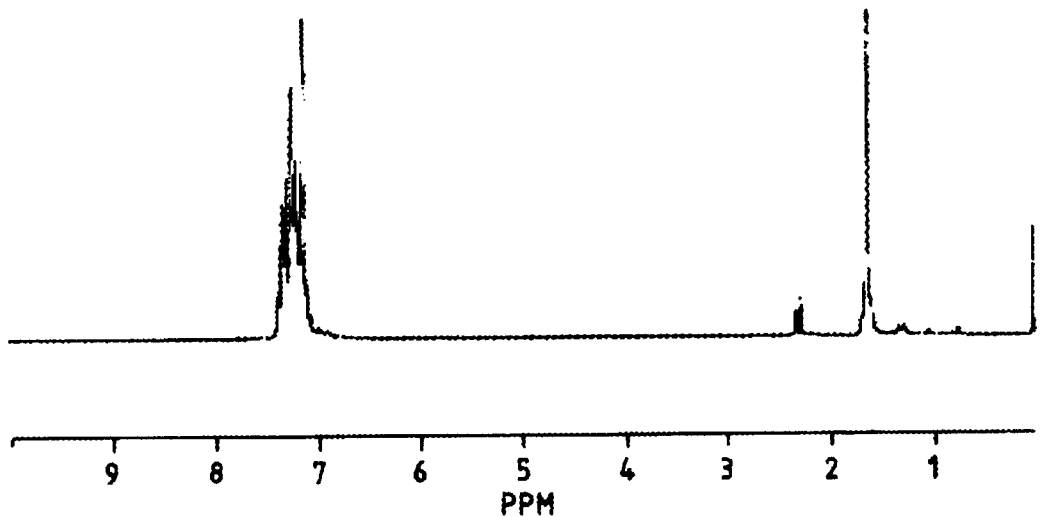

As another comparative compound herein, an oligomeric phosphoric acid ester compound II derived from a bisphenol-A was used. It was CR-741S supplied from Daihachi Chemical Company (Japan), which comprised 3.5% by weight of a monomeric phosphoric acid ester compound, 86.7% by weight of an oligomeric phosphoric acid ester compound having a number average polymerization degree of 1, and 9.8% by weight of an oligomeric phosphoric acid ester compound having a number average polymerization degree of not less than 2. This phosphoric acid ester compound II had characteristics as listed below. The results of IR and NMR analysis are shown in FIGS. 4a and 4b, respectively.

Characteristics of Phosphoric Acid Ester Compound II

Appearance: Transparent and viscous liquid phase
Phosphorus content: 8.9%
Acid value (KOHmg/g): 0.1
LC data: m is 0; 3.5%,
m is 1; 86.7%
m is 2 or more; 9.8%.
(m represents a polymerization degree)

B. Thermoplastic Resin (B-1) Polycarbonate Resin (PC)

A polycarbonate of bisphenol-A type having a weight average molecular weight of 25,000 was used.

(B-2) Rubber Modified Styrene Base Graft Copolymer (ABS)

To a mixture of 36 parts by weight of styrene, 14 parts by weight of acrylonitrile, and 150 parts by weight of deionized water, butadiene rubber latex was added so that the content of the butadiene became 45 parts by weight based on total weight of monomers. As additives, 1.0 parts by weight of calcium oleate, 0.4 parts by weight of cumenhydroperoxide and 0.3 parts by weight of a mercaptane base chain transferring agent were further added to the mixture and reacted for 5 hours while keeping a temperature at 75° C. to obtain ABS graft latex. To the resulting polymeric latex, a 1% solution of sulfuric acid was added, solidified and dried to obtain a graft copolymer resin as powder.

(B-3) Vinyl Aromatic Copolymer Resin (SAN)

71 parts by weight of styrene, 29 parts by weight of acrylonitrile and 120 parts by weight of deionized water were mixed together. As additives, 0.2 parts by weight of azobisisobutylonitrile, 0.3 parts by weight of a mercaptane based chain transferring agent and 0.5 parts by weight of tricalcium phosphate were added to the mixture. By conducting suspension polymerization, the SAN copolymer was prepared. This raw SAN copolymer was washed, drained and dried to obtain the pure SAN copolymer as powder.

(B-4) Polyphenylene Ether Resin (PPE)

As a polyphenylene ether resin, PPE P401 produced by Asahi Kasei Company (Japan) was used.

(B-5) High Impact Polystyrene Resin (HIPS)

As a high impact polystyrene resin, HI-1190F produced by Cheil Industries Inc. (Republic of Korea) was used.

(C) Fluorinated Polyolefinic Resin

As a fluorinated polyolefinic resin, Teflon 7AJ produced by Du Pont Company (U.S.A.) was used.

EXAMPLES

The above described components were mixed in a conventional mixer according to the compositions listed in Tables 1 to 3 below. Also, an antioxidant and thermal stabilizer were added to the mixtures. The mixtures were extruded using a twin-screw extruder with L/D=35 and Φ=45 mm, and formed specimens at an injection molding temperature of 220 to 280° C. for measuring mechanical properties and flame retardancy. The specimens were post-treated by leaving them for 48 hours at a temperature of 23° C. and a relative humidity of 50%. Then the specimens were measured for properties such as flame retardancy, melt flow rate and heat distortion temperature and the like.

Methods for Measuring the Properties of the Compositions

Flame retardancy: Evaluated using a specimen having a thickness of 1.6 mm according to the criterion specified in UL 94 VB.

Average combustion time and maximum single combustion time: Evaluated according to the criterion specified in UL 94.

Melt flow rate: Evaluated according to ASTM D1238.

Heat distortion temperature: evaluated at a load of 18.6 kgf according to ASTM D648.

TABLE 1

| Components | Ex. 1 | Comp. Ex. 1 | Ex. 2 | Comp. Ex. 2 |
|---|---|---|---|---|
| (A-1) Phosphoric acid ester morpholide compound I | 13 | — | — | — |
| (A-2) Phosphoric acid ester morpholide compound II | — | — | 13 | — |
| (A-3) Phosphoric acid ester compound I | — | 13 | — | — |
| (A-4) Phosphoric acid ester compound II | — | — | — | 13 |
| (B-1) Polycarbonate resin | 75 | 75 | 75 | 75 |
| (B-2) Rubber modified graft copolymer | 13 | 13 | 13 | 13 |
| (B-3) Vinyl aromatic copolymer | 12 | 12 | 12 | 12 |
| (C) Fluorinated polyolefinic resin | 0.5 | 0.5 | 0.5 | 0.5 |
| UL-94 flame retardancy (1/16") | V-0 | V-0 | V-0 | V-1 |
| Average combustion time (sec) | 2.3 | 3.2 | 2.9 | 5.9 |
| Maximum single combustion time (sec) | 3 | 7 | 4 | 16 |
| Melt flow rate (g/10 min)[1] | 27 | 22 | 24 | 18 |
| Heat distortion Temperature (° C.) | 91 | 85 | 94 | 90 |

[1]Evaluated under a condition of a temperature of 220 using a load of 10 kg

Example 1 and Comparative Example 1 are to compare the results of using the polyphosphate ester morpholide composition derived from resorcinol with the results obtained from using the oligomeric phosphoric acid ester compound derived from resorcinol as a flame retardant agent in a polycarbonate base resin blend. As shown in Table 1, flame retardancy was equal in both examples but heat resistance and melt flow rate were better in Example 1. Also, combustion time was shorter in Example 1.

Example 2 and Comparative Example 2 are to compare the results of using the polyphosphate ester morpholide composition derived from bisphenol-A with the results obtained by using the oligomeric phosphoric acid ester compound that was derived from bisphenol-A as a flame retardant agent in a polycarbonate resin blend. As shown in Table 1, all of the flame retardancy, heat resistance and melt flow rate were better in Example 2.

TABLE 2

| Components | Ex. 3 | Comp. Ex. 3 | Ex. 4 | Comp. Ex. 4 |
|---|---|---|---|---|
| (A-1) Phosphoric acid ester morpholide compound I | 16 | — | — | — |
| (A-2) Phosphoric acid ester morpholide compound II | — | — | 11 | — |
| (A-3) Phosphoric acid ester compound I | — | 16 | — | — |
| (A-4) Phosphoric acid ester compound II | — | — | — | 11 |
| (B-4) Polyphenylene ether resin | 50 | 50 | 75 | 75 |
| (B-5) High impact polystyrene base resin | 50 | 50 | 25 | 25 |
| (C) Fluorinated polyolefinic resin | 0.1 | 0.1 | 0.1 | 0.1 |
| UL-94 flame retardancy (1/16") | V-0 | V-1 | V-0 | V-1 |
| Average combustion time (sec) | 2.8 | 5.5 | 2.5 | 5.8 |
| Maximum single combustion time (sec) | 5 | 17 | 4 | 20 |
| Melt flow rate (g/10 min)[1] | 17 | 13 | 7 | 5 |
| HDT (° C.) | 86 | 82 | 126 | 121 |

[1]evaluating under a condition of a temperature of 250 using a load of 10 kg

Example 3 and Comparative Example 3 are to compare the results of using the phosphate ester morpholide composition derived from resorcinol with results obtained by the oligomeric phosphoric acid ester compound derived from resorcinol as a flame retardant agent in a polyphenylene ether base resin blend. As shown in Table 2, by using the polyphosphate ester morpholide compositions according to the present invention (compound (A-1)), good flame retardancy can be achieved with superiority in heat resistance and melt flow rate.

Example 4 and Comparative Example 4 are to compare the results of using the polyphosphate ester morpholide composition derived from bisphenol-A with the results obtained by using the oligomeric phosphoric acid ester compound that was derived from bisphenol-A as a flame retardant agent in a polyphenylene ether base resin blend. In these examples it was again shown that flame retardancy, heat resistance and melt flow rate were improved when using the polyphosphate ester morpholide composition in accordance with the present invention (compound (A-2)).

TABLE 3

| Components | Ex. 5 | Comp. Ex. 5 |
|---|---|---|
| (A-1) Phosphoric acid ester morpholide compound I | 17 | — |
| (A-3) Phosphoric acid ester compound I | — | 17 |
| (B-2) Rubber modified graft copolymer | 35 | 35 |
| (B-3) Vinyl aromatic copolymer | 35 | 35 |
| (B-4) Polyphenylene ether resin | 30 | 30 |
| (C) Fluorinated polyolefinic resin | 0.2 | 0.2 |
| UL-94 flame retardancy (1/16") | V-1 | X(HB) |
| Average combustion time (sec) | 18 | 28 |
| Maximum sing combustion time (sec) | 25 | 48 |
| Melt flow rate (g/10 min)[1] | 68 | 59 |
| HDT (° C.) | 78 | 74 |

[1]evaluating under a condition of a temperature of 220 using a load of 10 kg

Example 5 and Comparative Example 5 are to compare the results of using the polyphosphate ester morpholide composition derived from resorcinol with the oligomeric phosphoric acid ester compound derived from resorcinol as a flame retardant agent in a rubber modified graft copolymer/vinyl aromatic copolymer/polyphenylene ether resin blend. In these comparisons, it is again shown that flame retardancy, heat resistance and melt flow rate were better in Example 5.

As described above, in accordance with the present invention, by using a polyphosphate ester morpholide composition as a flame retardant agent added to the thermoplastic resin, it is possible to achieve improvement in flame retardancy even when using a small amount. Also, it is possible to provide a flame retardant thermoplastic resin composition with improvement in balance of properties such as flame retardancy, thermal stability, workability, impact strength, heat resistance, appearance and the like.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

What is claimed:

1. Compositions comprising mixtures of polyphosphate ester morpholides represented by the following general formula I:

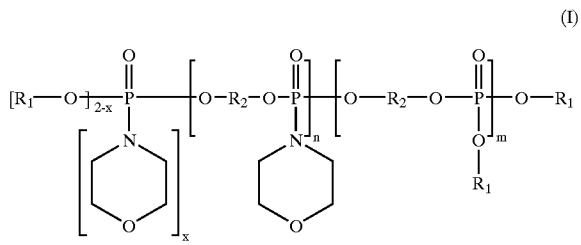

(I)

in which X is 1 or 2; $R_1$ is a $C_6$–$C_{20}$ aryl group, an alkyl substituted $C_6$–$C_{20}$ aryl group; $R_2$ is a $C_6$–$C_{30}$ arylene group or an alkyl substituted $C_6$–$C_{30}$ arylene group; n is the average number of morpholide repeating units, m is the average number of $R_1$ repeating units, and n+m is 1 to 5.

2. Compositions comprising mixtures of polyphosphate ester morpholides represented by the following general formula I:

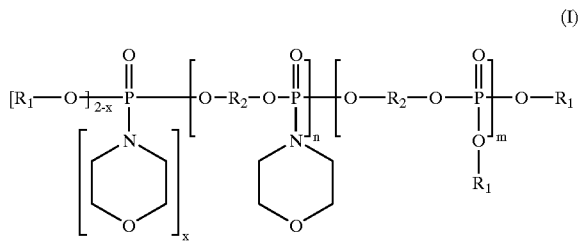

(I)

in which X is 1 or 2; $R_1$ is a phenyl group or a phenyl group substituted with methyl, ethyl, propyl, isopropyl, butyl, sec-butyl, tert-butyl, isobutyl, isoamyl, or tert-amyl; $R_2$ is a residue derived from resorcinol, hydroquinone, bisphenol-A or substituted resorcinol, hydroquinone, or bisphenol-A each having at least one methyl, ethyl, or t-butyl substituent; n is the average number of morpholide repeating units, m is the average number of $R_1$ repeating units, and n+m is 1 to 5.

3. Compositions according to claim 2 wherein $R_1$, is a phenyl group, or a phenyl group substituted with methyl, ethyl, isopropyl or tert-butyl group.

4. Compositions according to claim 2 wherein $R_2$ is a residue derived from resorcinol, hydroquinone, or bisphenol-A.

5. Compositions according to claim 2 wherein n+m is 1–3.

6. Compositions according to claim 2 wherein n+m is 1 or 2.

7. Compositions according to claim 2 wherein the mixture represented by formula (I) comprises about 0 to 20% by weight having m+n=0, about 30 to 100% by weight having m+n=1, and about 0 to 50% by weight having m+n=2 or more.

8. Compositions comprising at least one polyphosphate ester morpholide having the following general formula II:

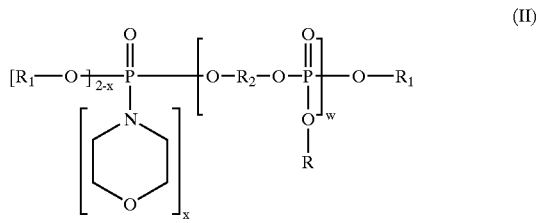

(II)

wherein x is 1 or 2, R is a morpholino group or the same group as $R_1$, w is 1 to 5, $R_1$ is a $C_6$–$C_{20}$ aryl group, an alkyl substituted $C_6$–$C_{20}$ aryl group or a derivative thereof; $R_2$ is a $C_6$–$C_{30}$ arylene group, an alkyl substituted $C_6$–$C_{30}$ arylene group or a derivative thereof.

9. Compositions comprising at least one polyphosphate ester morpholides represented by the following general formula II:

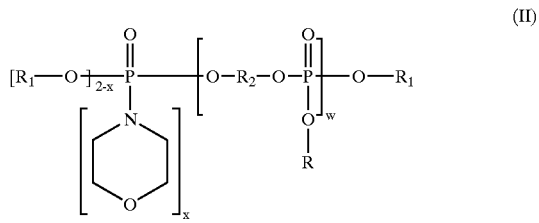

(II)

wherein x is 1 or 2, R is a morpholino group or the same group as $R_1$, w is 1 to 5; $R_1$ is a phenyl group or a phenyl group substituted with methyl, ethyl, propyl, isopropyl, butyl, sec-butyl, tert-butyl, isobutyl, isoamyl, tert-amyl; $R_2$ is a residue derived from resorcinol, hydroquinone, or bisphenol-A or substituted resorcinol, hydroquinone, or bisphenol-A each having at least one methyl, ethyl, or t-butyl substituent.

10. Compositions according to claim 9 wherein $R_1$ is a phenyl group, or a phenyl group substituted with a methyl, ethyl, isopropyl or tert-butyl group.

11. Compositions according to claim 9 wherein $R_2$ is a residue derived from resorcinol, hydroquinone, or bisphenol-A.

12. Compositions according to claim 9 wherein $R_2$ is a residue derived from resorcinol, hydroquinone, or bisphenol-A each having at least one methyl, ethyl, and t-butyl substituent.

13. Compositions comprising at least one polyphosphate ester morpholide wherein the compositions are prepared by the reaction of an aromatic alcohol, morpholine, phosphorus oxychloride ($POCl_3$), and a dihydroxy arylene compound in the presence of a catalyst wherein the aromatic alcohol is phenol, methyl phenol, dimethyl phenol, ethyl phenol, diethyl phenol, propyl phenol, isopropyl phenol, butyl phenol, sec-butyl phenol, tert-butyl phenol, di-t-butyl phenol, isobutyl phenol, isoamyl phenol, or tert-amyl phenol and the dihydroxy arylene compound is resorcinol, hydroquinone, bisphenol-A, or substituted resorcinol, hydroquinone, or bisphenol-A each having at least one methyl, ethyl, or t-butyl substituent.

14. Compositions according to claim 13 wherein the polyphosphate morpholide compositions are prepared by first reacting the aromatic alcohol and morpholine with phosphorus oxychloride ($POCl_3$) in the presence of an appropriate catalyst to obtain an aryl morpholino chlorophosphate and the aryl morpholino chlorophosphate is then reacted with the dihydroxy arylene compound in the presence of a catalyst.

15. Compositions according to claim 13 wherein the dihydroxy arylene compound is resorcinol, hydroquinone, or bisphenol-A.

16. Compositions according to claim 13 wherein the substituted resorcinol, hydroquinone, or bisphenol-A is resorcinol, hydroquinone, or bisphenol-A having at least one methyl, ethyl, or t-butyl substituent.

17. Compositions according to claim 13 wherein the polyphosphate morpholide compositions are prepared by first reacting phosphorus oxychloride ($POCl_3$) with the dihydroxy arylene compound in the presence of an appropriate catalyst and then reacting the resulting product with the aromatic alcohol and morpholine in the presence of a catalyst.

18. Compositions according to claim 1 wherein the alkyl substituted groups are resorcinol, hydroquinone, or bisphenol-A having one or two methyl, ethyl, or t-butyl substituent.

19. Compositions according to claim 2 wherein $R_2$ is a residue derived from resorcinol, hydroquinone, or bisphenol-A each having two methyl, ethyl, and t-butyl substituents.

20. Compositions according to claim 9 wherein $R_2$ is a residue derived from resorcinol, hydroquinone, or bisphenol-A each having two methyl, ethyl, and t-butyl substituents.

\* \* \* \* \*